United States Patent
Carinci et al.

(10) Patent No.: US 10,712,417 B2
(45) Date of Patent: Jul. 14, 2020

(54) METHOD AND APPARATUS FOR EXECUTING AN ACCELERATED MAGNETIC RESONANCE SCAN

(71) Applicant: Siemens Healthcare GmbH, Erlangen (DE)

(72) Inventors: Flavio Carinci, Erlangen (DE); Mario Zeller, Erlangen (DE)

(73) Assignee: Siemens Healthcare GmbH, Erlangen (DE)

(*) Notice: Subject to any disclaimer, the term of this patent is extended or adjusted under 35 U.S.C. 154(b) by 153 days.

(21) Appl. No.: 16/100,523

(22) Filed: Aug. 10, 2018

(65) Prior Publication Data
US 2019/0049541 A1 Feb. 14, 2019

(30) Foreign Application Priority Data
Aug. 11, 2017 (EP) .................................. 17185859

(51) Int. Cl.
*G01R 33/561* (2006.01)
*G01R 33/483* (2006.01)
*A61B 5/055* (2006.01)
*G01R 33/48* (2006.01)
*G01R 33/54* (2006.01)
G01R 33/565 (2006.01)
A61B 90/00 (2016.01)
(Continued)

(52) U.S. Cl.
CPC .......... *G01R 33/5611* (2013.01); *A61B 5/055* (2013.01); *G01R 33/4818* (2013.01); *G01R 33/4835* (2013.01); *G01R 33/543* (2013.01); *A61B 2090/374* (2016.02); *G01R 33/246* (2013.01); *G01R 33/4814* (2013.01); *G01R 33/5617* (2013.01); *G01R 33/56509* (2013.01); *G01R 33/56563* (2013.01); *G01R 33/583* (2013.01)

(58) Field of Classification Search
CPC ............ G01R 33/5611; G01R 33/4818; G01R 33/543; A61B 5/055
USPC ........................................................ 324/309
See application file for complete search history.

(56) References Cited

U.S. PATENT DOCUMENTS 10,120,050 B2 * 11/2018 Feiweier ................. G01R 33/56
10,557,903 B2 * 2/2020 Carinci .............. G01R 33/4835
(Continued)

OTHER PUBLICATIONS

Breuer et. al.: "Controlled Aliasing in Parallel Imaging Results in Higher Acceleration (CAIPIRINHA) for Multi-Slice Imaging"; in: Magnetic Resonance in Medicine; vol. 53; pp. 684-691; (2005).
(Continued)

*Primary Examiner* — Patrick Assouad
*Assistant Examiner* — Demetrius R Pretlow
(74) *Attorney, Agent, or Firm* — Schiff Hardin LLP

(57) ABSTRACT

In a method and apparatus for creating magnetic resonance data of at least two simultaneously manipulated, non-overlapping slices of an examination object by a parallel acquisition technique, reference data are acquired such that, between acquisition of slice scan data of a slice scan data set in which the scan data of all simultaneously manipulated slices are incorporated in an overlaid manner, and its associated reference data, no slice scan data of a different slice scan data set are acquired. A high level of robustness with respect to movements of the examination object is thereby achieved.

13 Claims, 6 Drawing Sheets

(51) Int. Cl.
*G01R 33/24* (2006.01)
*G01R 33/58* (2006.01)

(56) References Cited

U.S. PATENT DOCUMENTS

| | | | |
|---|---|---|---|
| 2012/0146640 A1* | 6/2012 | Kusahara | G01R 33/56554 |
| | | | 324/309 |
| 2014/0218026 A1* | 8/2014 | Moeller | G01R 33/4835 |
| | | | 324/309 |
| 2014/0247046 A1* | 9/2014 | Grinstead | G01R 33/4835 |
| | | | 324/309 |
| 2015/0084629 A1* | 3/2015 | Porter | G01R 33/54 |
| | | | 324/309 |
| 2015/0301143 A1 | 10/2015 | Banerjee et al. | |
| 2015/0346300 A1* | 12/2015 | Setsompop | G01R 33/4828 |
| | | | 324/309 |
| 2017/0038450 A1* | 2/2017 | Hoge | G01R 33/4835 |
| 2017/0123029 A1* | 5/2017 | Bhat | G01R 33/56581 |
| 2017/0146631 A1* | 5/2017 | Beck | G01R 33/4833 |
| 2017/0261582 A1* | 9/2017 | Blasche | G01R 33/4835 |
| 2017/0322280 A1 | 11/2017 | Carinci et al. | |
| 2018/0017655 A1* | 1/2018 | Zeller | G01R 33/583 |
| 2018/0074147 A1 | 3/2018 | Carinci et al. | |
| 2018/0095150 A1 | 4/2018 | Zeller | |
| 2018/0267123 A1* | 9/2018 | Beck | G01R 33/5611 |

OTHER PUBLICATIONS

Zhu et al. "Simultaneous Multi-slice Flyback Echo Planar Imaging with Auto-calibration"; Proceedings of the International Society for Magnetic Resonance in Medicine; 21st Annual Meeting & Exhibition; (2013).

Wang, et al. "Improving Slice Resolution of Knee Imaging Using Multiband Slice Accelerated TSE"; Proceedings of the International Society for Magnetic Resonance in Medicine; 23rd Annual Meeting & Exhibition; (2015).

Zahneisen, et al. "Three-Dimensional Fourier Encoding of Simultaneously Excited Slices: Generalized Acquisition and Reconstruction Framework", Magnetic Resonance in Medicine, vol. 71, pp. 2071-2081; (2014).

Setsompop, et al.: "Blipped-Controlled Aliasing in Parallel Imaging for Simultaneous Multislice Echo Planar Imaging with Reduced g-Factor Penalty"; Magnetic Resonance in Medicine; vol. 67; pp. 1210-1224; (2012).

Bhat, et. al.: "Motion Insensitive ACS Acquisition Method for in-plane and Simultaneous Multi-Slice Accelerated EPI"; in: Proc. Intl. Soc. Mag. Reson. Med.; vol. 22; p. 0644; (2014).

Schulz, et al. "Clinical application of Half Fourier Acquisition Single Shot Turbo Spin Echo (HASTE) imaging with multiband (MB) excitation and PINS refocusing pulses"; Proceedings of the International Society for Magnetic Resonance in Medicine, 25th Annual Meeting & Exhibition; No. 4620; (2017).

* cited by examiner

METHOD AND APPARATUS FOR EXECUTING AN ACCELERATED MAGNETIC RESONANCE SCAN

BACKGROUND OF THE INVENTION

Field of the Invention

The invention concerns a method and apparatus for executing an accelerated magnetic resonance scan, in particular a single-shot method accelerated by slice multiplexing

Description of the Prior Art

Magnetic resonance (MR) is a known modality with which images of the inside of an examination object can be generated. Simply explained, the examination object is positioned in a magnetic resonance scanner in a strong, static, homogeneous, basic magnetic field, also called a $B_0$ field, having field strengths of 0.2 tesla to 7 tesla and more for this purpose, so nuclear spins in the object are oriented along the basic magnetic field. Radio-frequency excitation pulses (RF pulses) are radiated into the examination object in order to trigger nuclear spin resonances. The triggered nuclear spin resonances are detected as echo signals, which are stored in a memory in a form known as k-space data, using, for example, a multi-dimensional Fourier transform, MR images are reconstructed (or spectroscopy data are determined) from k-space data. For spatial encoding of the scan data, rapidly switched magnetic gradient fields are overlaid on the basic magnetic field.

There are basically two ways of generating echo signals after an excitation of the nuclear spins. The excited nuclear spins can be manipulated by switching dephasing and rephasing gradients such that the MR signal decays more quickly than accounted for by the T2*decay inherent to the scanned tissue. After a certain time, the echo time (TE), following the RF excitation pulse, the signal what is known as a gradient echo (GRE), which is to be detected. Sequences of this kind are conventionally called GRE sequences. Alternatively, by radiation of at least one RF refocusing pulse at a time following radiation of an RF excitation pulse, again called the echo time, a signal is known as a spin echo (SE) can be generated detected, but its amplitude is reduced according to the T2 decay inherent to the scanned tissue. Sequences of this kind are conventionally called SE sequences. There are also sequences that generate gradient echoes as well as spin echoes, for example (true)FISP sequences. In each case, the excitation and scanning (detection) of the generated echo signals is optionally repeated for each sequence until (for example by switching different gradients for spatial encoding) the desired number of echo signals is scanned and stored in k-space, in order to be able to reconstruct an image of the examination object.

Among the SE sequences, in particular the TSE sequences (TSE: "Turbo Spin Echo"), which are also known by the name FSE ("Fast Spin Echo") or RARE ("Rapid Acquisition with Refocused Echoes") sequences are common in clinical application. The advantage of the TSE sequences compared to the "simple" SE sequence is that, after an RF excitation pulse, a plurality of refocusing pulses are switched, and that, as a result, a number of spin echo signals is also generated. Data acquisition is accelerated as a result.

In a technique known as the "single-shot" method, all of k-space data to be acquired, for example for imaging a slice of an examination object, can be acquired after just one RF excitation by an RF excitation pulse.

One example of a single-shot TSE sequence of this kind is the HASTE sequence ("Half-Fourier Acquisition Single-shot Turbo spin Echo imaging") in which a "partial Fourier" method, in particular the Half-Fourier method, is used in order to reduce k-space data that need to be acquired. The symmetry of k-space with respect to complex conjugation is used to derive non-scanned (interpolated) k-space data from the scanned k-space data. All k-space data of a slice to be imaged that are necessary for this method thus can be acquired after just one excitation pulse. If multiple slices of an examination object are to be scanned, for example, all necessary k-space data of a slice can be acquired by the HASTE sequence after just one excitation. HASTE techniques are therefore conventionally used for scans of the thorax or abdomen where they allow coverage of relatively large volumes of interest (VOI) within one of more breath-holding phases with a reduced sensitivity to physiological movements of the examination object.

HASTE acquisition techniques are also known, inter alia, by the acronyms SS-FSE (single-shot Fast Spin Echo), SSH-TSE (Single-SHot Turbo Spin Echo), UFSE (Ultra-Fast Spin Echo), Single-Shot Fast SE or FASE or Super-FASE (Fast Advanced Spin Echo).

FIG. 1 is a schematic sequence timing diagram of a HASTE sequence of this kind. As already mentioned, after an excitation pulse RF1, a number of refocusing pulses RF2 is switched so as to generate a number of spin echo signals which are each produced between the refocusing pulses RF2 (not shown). In order to limit the excitation to spins of a particular slice, a corresponding slice selection gradient GS can be simultaneously switched (activated) with each excitation pulse RF1 and refocusing pulse RF2. Frequency encoding gradients GF and phase encoding gradients GP can be switched for further spatial encoding. With HASTE, some (as a rule, nearly half) of the phase encoding gradients GP can be omitted, as is indicated in FIG. 1 by the asymmetric arrangement of the phase encoding gradients GP. The corresponding, "missing" spin echo signals can, as stated, be supplemented by a partial-Fourier method. The illustrated asymmetric arrangement of the phase encoding gradients GP, in which after scanning of the echo signals in k-space center (GP=0) a larger number of echo signals is scanned than before the scanning of k-space center, is advantageous in order to keep the echo times as short as possible for which the region of k-space center (low amplitudes of the phase encoding gradients GP) is scanned (filled with acquired data). In this way, the echo signals of the region of k-space center are attenuated less strongly according to the T2 decay than with a different arrangement, which only scans the region of k-space center at later echo times.

In addition to the partial Fourier methods, further, so-called parallel acquisition techniques (for example GRAPPA ("GeneRalized Autocalibrating Partially Parallel Acquisition") and SENSE ("SENSitivity Encoding") are known, with which acquisition times required for acquiring the desired data may be shortened. As with partial-Fourier methods, only parts of the echo signals that are actually to be acquired as k-space data according to the Nyquist condition are scanned. In contrast to the partial-Fourier methods, as a rule the non-scanned parts are more uniformly distributed over region of k-space to be scanned according to Nyquist in the case of parallel acquisition techniques. For example, only every other (alternating) k-space line is scanned. Furthermore, the "missing" k-space data are reconstructed with the use of coil sensitivity data in the case of parallel acquisition techniques. The coil sensitivity data of the reception coils used during acquisition of the scan data are determined from reference data, which completely (according to the Nyquist criterion) sample at least one region of k-space to be scanned, usually the central region.

The desire for ever faster MR scans in the clinical field is currently leading to development of methods in which a number of images are simultaneously acquired. In general, these methods may be characterized by the transverse magnetization of at least two slices being simultaneously used for the imaging process ("multi-slice imaging", "slice multiplexing") at least during part of the scan. In contrast thereto, in the case of established "multi-slice imaging", the signals of at least two slices are acquired alternately, in other words completely independently of each other, with a correspondingly longer scan time.

Known methods for this are Hadamard coding, methods with simultaneous echo refocusing, methods with broadband data acquisition, and methods which use parallel imaging in the slice direction. The last-mentioned methods also include, for example, the CAIPIRINHA technique, as is described by Breuer et al. in "Controlled Aliasing in Parallel Imaging Results in Higher Acceleration (CAIPIRINHA) for Multi-Slice Imaging", Magnetic Resonance in Medicine 53, 2005, pages 684-691, and the blipped CAIPIRINHA technique, as is described by Setsompop et al. in "Blipped-Controlled Aliasing in Parallel Imaging for Simultaneous Multislice Echo Planar Imaging With Reduced g-Factor Penalty", Magnetic Resonance in Medicine 67, 2012, pages 1210-1224.

Particularly with the last-mentioned slice multiplexing methods, a multi-band RF pulse is used to excite two or more slices at the same time (simultaneously) or to manipulate them in some other way, for example to refocus or saturate. A multi-band RF pulse is, for example, produced by multiplexing individual RF pulses, which would be used for exciting spins in the individual slices to be excited simultaneously. For example, a baseband-modulated multi-band RF pulse is obtained by an addition of the pulse waveforms of the individual RF pulses by multiplexing. The spatial encoding of the acquired signals is achieved essentially by a common gradient switching process in two directions (two-dimensional gradient encoding). The effect of the multi-band RF pulse is thereby spatially selectively limited to the desired slices.

The resulting signals from all excited slices collapsed in one data set, acquired by a number of receiving antennas, and are then separated according to the individual slices with the use of parallel acquisition techniques.

As noted above, the acquisition time required for acquiring the desired data can generally be reduced by parallel acquisition techniques by undersampling (sampling that is not complete according to Nyquist), in other words undersampling of k-space.

With slice multiplexing methods, parallel acquisition techniques are used to separate the scan data simultaneously acquired for various slices again. Reference data has to be acquired for all relevant slices. Usually this occurs during the course of a reference scan that has to be carried out in addition to the diagnostic scan. The reference scan individually scans the reference data for each desired slice.

In order to be able to separate the resulting signals of the various slices, a different phase in each case is impressed on the individual RF pulses before multiplexing, for example by adding a phase amount, the added phase amount increasing linearly (for example with k-space coordinate in the phase encoding direction ($k_y$)). A different phase increase thus can be impressed on each slice, so the slices are shifted toward each other in the image domain. This shift is controlled by the FOV (field of view) shift factor. How an optimum FOV shift factor can be determined is described, for example, in DE102016218955.

In the CAIPIRINHA methods described in the aforementioned articles by Breuer et al. and Setsompop et al., by switching additional gradient blips or by additional modulation of the phases of the RF pulses of the multi-band RF pulses, alternating further phase shifts are impressed between the simultaneously excited slices, and these generate shifts in the image space. These additional shifts in the image space improve the quality of the separation of the signals of the slices, particularly if the coil sensitivities have such slight differences in the sensitivity profiles of the individual used coils that they are not adequate for reliable separation of the slices. Artifacts in the image data ultimately reconstructed from scanned scan data are therefore reduced.

The reference data, from which the sensitivity data required for the separation of the slices and/or supplementing of the missing scan points are obtained, conventionally has to be additionally scanned for each slice multiplexing scan.

If this kind of reference data are acquired with a different sequence type than the scan data of the actual scan that is to be completed, this can lead to artifacts during reconstruction of the scan data, due to potentially different contrasts and/or different sensitives to various interferences. Non-coincidence of the instants at which the reference data are acquired compared to the actual scan data (for example due to (undesirable) movements of the examination object), can also lead to artifacts during reconstruction. This is also a reason why slice multiplexing methods are already combined with a large number of different sequence types, inter alia EPI and TSE, but a combination with single-shot TSE techniques has not as yet led to satisfactory results.

Furthermore, deviations in the scanning parameters used during acquisition of the reference data from the scanning parameters used in multi-band acquisition, in particular scanning parameters in respect of the properties of the RF excitation pulses and/or in respect of the readout process, such as the readout bandwidth, affect the quality of the separation of the slices and lead to undesirable artifacts. Various methods have been described from this point of view in United States Patent Application Publication No. 2018/0074147, with regard to the manner in which this kind of reference data can be obtained in addition to the multi-band scan data.

A method is described in DE102016207641 as to how reference data are acquired for single-slice scans following acquisition of scan data in order, for example, to reduce sensitivity to physiological movements. The reference data in each case are scanned only for the one scanned slice here, however.

SUMMARY OF THE INVENTION

An object of the invention is to make it possible to combine the advantages of single-shot methods, in particular HASTE, with the advantages of slice multiplexing without loss of quality.

An inventive method for creating magnetic resonance data of at least two non-overlapping slices of an examination object by a parallel acquisition technique has the following steps. A multi-band RF excitation pulse is radiated into, which simultaneously and selectively manipulates the magnetization of nuclear spins in at least two non-overlapping slices in the target volume. Echo signals generated by the multi-band RF excitation pulse are acquired from the at least two slices as slice scan data in a slice scan data set, so the slice scan data set includes scan data of all simultaneously manipulated slices. Reference data of the at least two slices are acquired such that, in a central region of k-space filled by the slice scan data and the reference data, overall there is a complete data set. The reference data for a slice scan data set are acquired such that, between acquisition of the slice scan data of the slice scan data set and acquisition of its associated reference data, no scan data of slices are acquired that are not included in the at least two slices of the slice scan data set. Calibration data are created from the complete data set. The slice scan data set is separated into single-slice scan data sets of the simultaneously manipulated slices using the calibration data. Image data are reconstructed from the single-slice scan data sets.

By acquiring the reference data so that no slice scan data of a different slice scan data set are acquired between acquisition of the slice scan data of the slice scan data set and its associated reference data, the method achieves a high level of robustness with respect to movements of the examination object. Due to the acquisition of the reference data and the acquisition of the associated slice scan data being close together in terms of time, the reference data are inherently acquired in the same movement state of the examination object as the slice scan data. Therefore, artifacts that occur due to different movement states for reference data and slice scan data are avoided.

This is advantageous particularly with single-shot TSE methods, which are otherwise particularly susceptible to movement-induced artifacts. The advantages of slice multiplexing methods, which require acquisition of reference data, thus can be combined with the advantages of single-shot methods.

Due to the acceleration of acquisition of the scan data that is possible with a slice multiplexing method, with single-shot methods a reduction in an overall breath-hold time required for complete data acquisition (for example in the case of abdominal HASTE examinations) can be achieved both for scans in which the patient only has to hold his or her breath once, as well as for scans in which the patient is to hold his or her breath several times for different scan processes in each case.

Even if it is not necessary or desirable to reduce the overall breath-hold time, the method described herein allows scan data to be acquired from more slices in the same breath-hold time, therefore enabling a higher slice coverage.

The method described herein therefore has advantages for patients with reduced breath-holding ability, since the method enables particular scans for these kinds of patients to be used that might otherwise not be useable, and also because, in any case, the comfort level is significantly increased for the patient due to the reduction in acquisition times and/or breath-hold times.

The method described herein can therefore ensure, in particular with MR scans in which there is a requirement for a patient to hold his breath for the duration of a data acquisition, that no great differences occur in the scanning conditions, in particular with respect to a breath-hold position of the patient, during acquisition of the (slice) scan data on the one hand and during acquisition of reference data, which is required for subsequent reconstruction of the image data, on the other hand. Undesirable artifacts are thereby efficiently avoided.

An inventive magnetic resonance system has a data acquisition scanner with a gradient unit, a radiofrequency unit and a control computer designed to execute the inventive method, having a radio-frequency transceiving controller with a multi-band RF pulse generator.

The present invention also encompasses a non-transitory, computer-readable data storage medium encoded with programming instructions (program code) that, when the storage medium is loaded into a control computer or computer system of a magnetic resonance apparatus, cause the computer or computer system to operate the magnetic resonance apparatus so as to implement any or all embodiments of the method according to the invention, as described above.

The advantages and explanations described with respect to the method apply analogously to the magnetic resonance apparatus and the electronically readable data storage medium as well.

DESCRIPTION OF THE PREFERRED EMBODIMENTS

FIGS. 2 to 5 contrast, as examples, various sampling patterns of k-space for GRAPPA-type parallel imaging techniques, each with a Cartesian sampling pattern. The $k_x$ direction is perpendicular to the sheet plane here and the sampling pattern is always the same in the $k_x$ direction if sampling occurs in the $k_x$ direction. The filled circles represent scanned k-space points, the empty circles missed k space points. The number of k space points that are actually to be scanned can be significantly higher than in the figures showing sampling patterns. The illustrated sampling patterns each show only the underlying sampling patterns.

Figure 1:
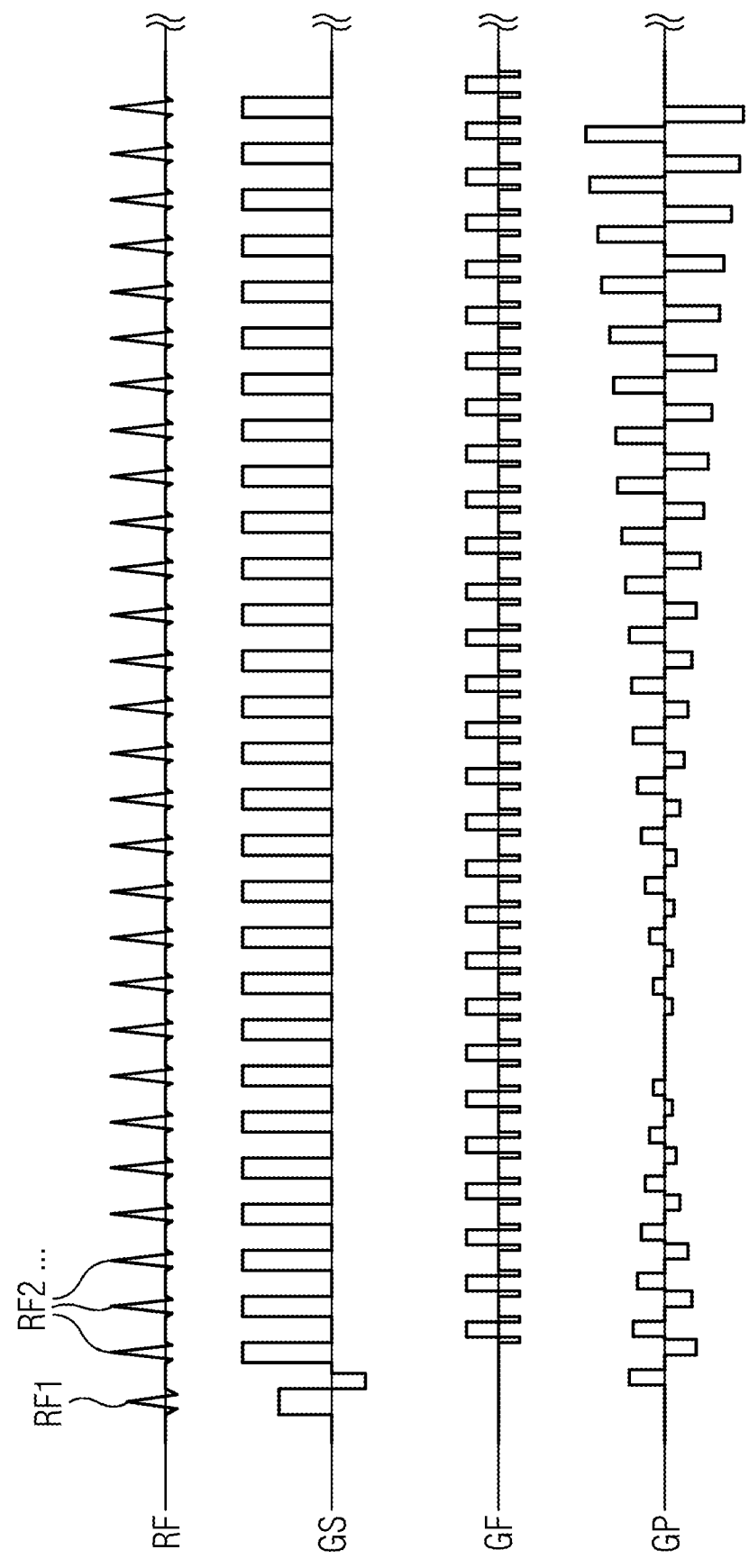
FIG. 1 is a schematic illustration of a HASTE sequence.
Figure 2:
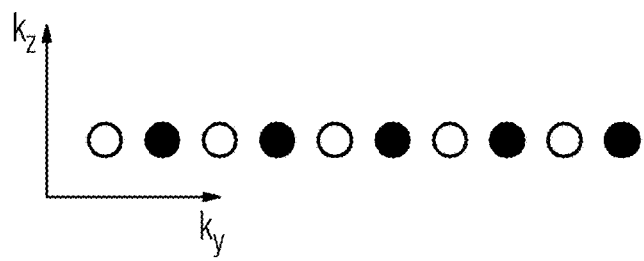
FIGS. 2-5 are shows schematic illustrations of various sampling patterns of k-space for parallel acquisition techniques.

FIG. 2 shows a conventional single-slice GRAPPA sampling in which every second k-space line in a spatial direction (here: the $k_y$ direction) is missing, and therefore only half of k-space points are scanned, and this corresponds to an acceleration factor of 2.

Figure 3:
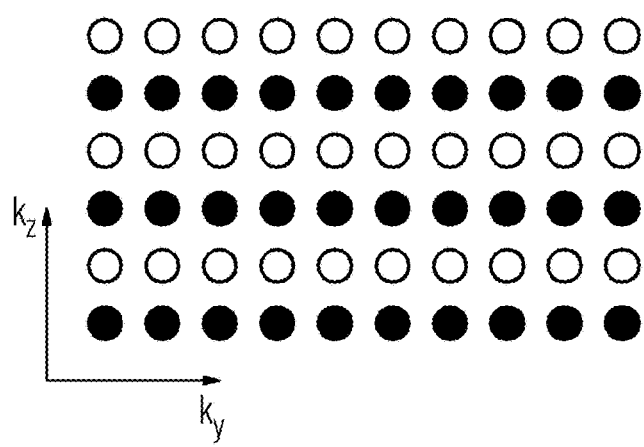

FIG. 3 shows a conventional three-dimensional (3D) GRAPPA sampling, which samples k-space lines in the ky-kx plane, and in which every second k-space line in a spatial direction (here: the kz direction) is missing, and therefore only half of k-space points are scanned, so an acceleration factor of 2 results here as well.

Figure 4:
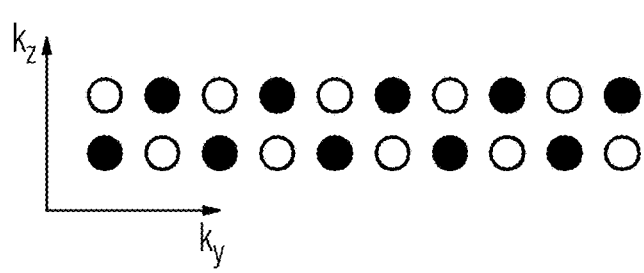

FIG. 4 illustrates the effect of the additional phase shifts on the sampling pattern of a two-dimensional (2D) slice multiplexing scan. Due to the additional phases, as are impressed for example in slice multiplexing CAIPIRINHA methods, the scanning points loaded with the additional phase are shifted in k-space. In the example illustrated in FIG. 4, every second k-space point in the $k_y$ direction is loaded with a phase which leads to a shift in the $k_z$ direction. How big this shift is in the $k_z$ direction depends on the impressed phase. This is also described for example in the article by Zahneisen et al.: "Three-Dimensional Fourier Encoding of Simultaneously Excited Slices: Generalized Acquisition and Reconstruction Framework", Magn. Reson. Med. 71, pages 2071-2081 (2014). A two-dimensional (2D) slice multiplexing scan with shifts impressed by additional gradients in the third (perpendicular to the 2D plane) k-space direction can therefore be considered analogously to a 3D CAIPIRINHA scan. A complete reference data set is required to reconstruct a data set acquired in this way. With the use of parallel acquisition techniques and on the basis of the reference data set the acquired scan data can be separated into the various slices and undersampled data of a slice can also be completed.

Figure 5:
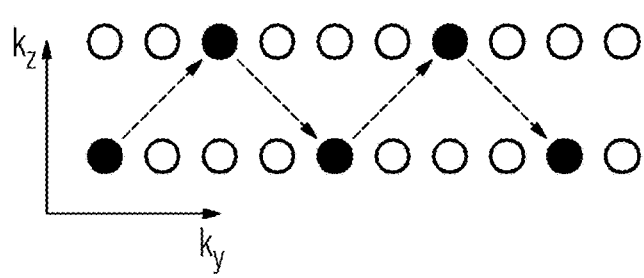

FIG. 5 illustrates a sampling pattern in which the sampling illustrated in FIG. 2 is combined with slice multiplexing as is shown in FIG. 4. Therefore, already only every other k-space point is scanned in the $k_y$ direction (as in FIG. 2) and, in addition, every other scanned k-space point is loaded with an additional phase, so there is a shift (here) in the $k_z$ direction. ("Other" meaning alternating scanning and not scanning).

If this sampling pattern is regarded like a 3D pattern, it follows that in every $k_y$ line, in each case only one k-space data point is acquired and the following three k-space data points are not acquired. Therefore, in each case three k-space points between two acquired k-space points have to be supplemented by reconstruction in each $k_y$ line to obtain a complete data set.

A sampling pattern of this kind can be achieved for example using a HASTE method with a multi-band RF excitation pulse, which excites two slices simultaneously, followed by a series of multi-band RF refocusing pulses, which refocus the spins in the two slices, and acquisition of the echo signals generated in this way as scan data sets in which the scan data of the slices is in overlaid form.

Figure 6:
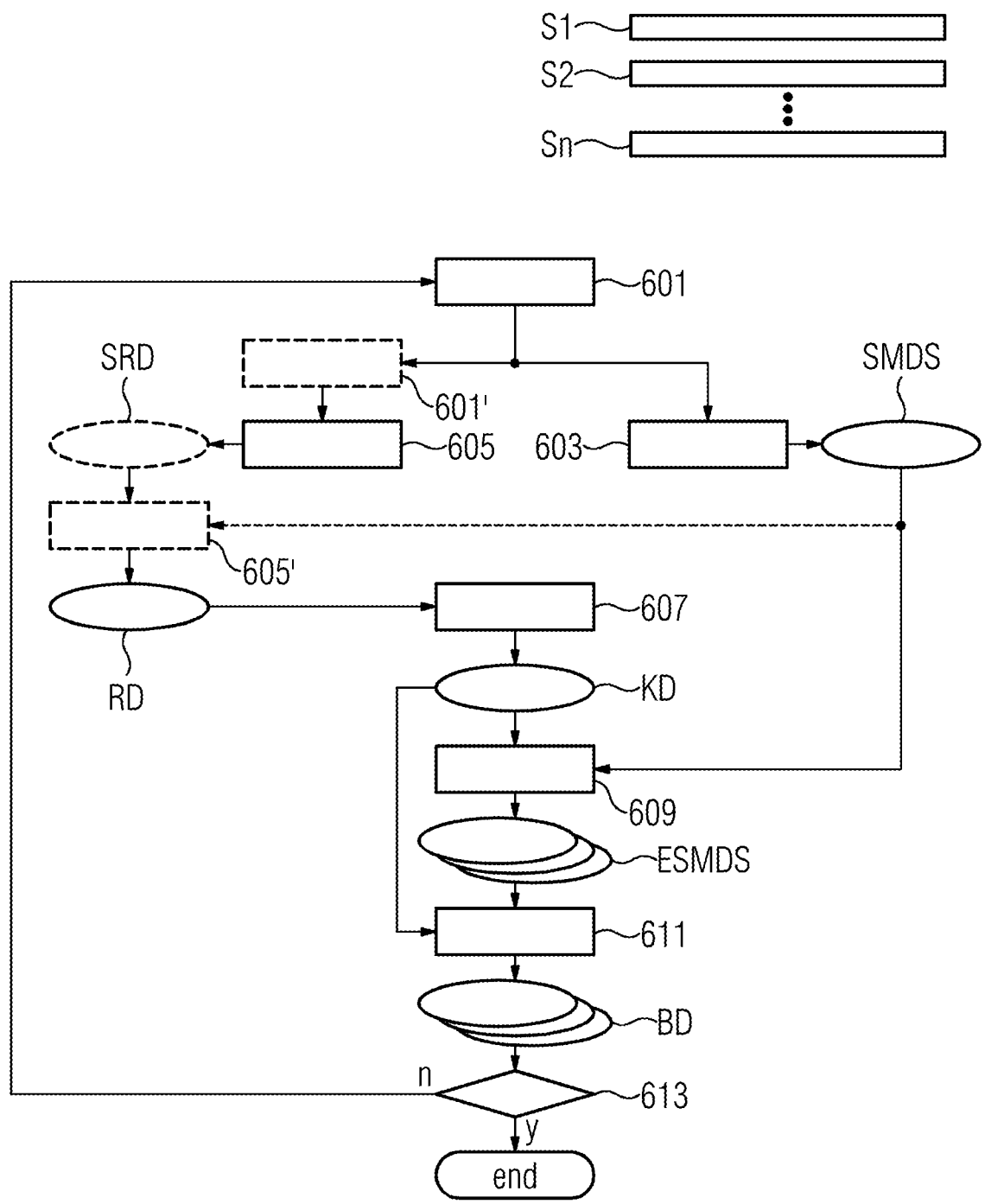
FIG. 6 is a schematic flowchart of the inventive method.

FIG. 6 is a flowchart of the inventive method for creating magnetic resonance data of at least two non-overlapping, in particular parallel, slices of an examination object by means of a parallel acquisition technique. A multi-band RF excitation pulse is radiated into a target volume (FOV) of an examination object (Block 601). The multi-band RF excitation pulse manipulates the magnetization of at least two non-overlapping slices S1, S2, . . . Sn simultaneously and selectively, in particular it excites the spins in the at least two non-overlapping slices S1, S2, . . . Sn simultaneously and selectively.

The echo signals generated by the multi-band RF excitation pulse from the at least two slices are acquired as slice scan data (Block 603) and are stored in a slice scan data set SMDS. The slice scan data matches the overlaid scan data acquired from the at least two slices. The slice scan data set SMDS therefore comprises scan data of all simultaneously manipulated slices. All echo signals of a slice scan data set SMDS can be acquired after a single multi-band RF pulse here (single-shot). The magnetic resonance data can be acquired here according to a turbo spin echo sequence, in particular according to a HASTE sequence.

Reference data RD of the at least two slices belonging to the slice scan data acquired in Block 603 is acquired in such a way (Block 605) that in a central region of k-space filled by the acquired slice scan data of the slice scan data set SMDS and the acquired reference data overall there is a complete data set according to Nyquist. Reference data RD for a slice scan data set SMDS is acquired such that between acquisition 603 of the slice scan data of the slice scan data set SMDS and acquisition 605 of its associated reference data RD, no slice scan data of a different slice scan data set are acquired. In other words, between acquisition 603 of the slice scan data of the slice scan data set SMDS and acquisition 605 of its associated reference data RD, no scan data of slices are acquired that are not included in the at least two slices of the slice scan data set. Acquisition 605 of the reference data RD therefore occurs after radiation 601 of the multi-band RF excitation pulse and at the latest immediately following acquisition 603 of the slice scan data.

Acquisition 605 of the reference data RD can occur after radiation of a further RF pulse. For example, acquisition 605 of the reference data RD can occur after radiation of a second multi-band RF pulse for simultaneous and selective manipulation of the at least two slices, wherein the reference data RD can be stored as slice reference data SRD, which contain the reference data of the at least two slices in an overlaid manner. The obtained slice reference data SRD can be separated into reference data RD, which in each case comprises only reference data of one of the at least two slices (Block 605'). In order to separate the slice reference data SRD into (single-slice) reference data RD, for example a Fourier transform can be used in a k-space direction, in which a shift was generated by additional gradients, as is described in the cited article by Zahneisen et al. Further explanations in this regard will be given below with reference to FIGS. 7 to 10.

It is also possible to carry out acquisition 605 of the reference data RD after radiation of single-slice RF excitation pulses for each of the at least two slices, with the reference data RD being acquired and stored directly as respective reference data RD for each of the at least two slices. Further explanations in this regard will be given below with reference to FIGS. 11 and 12.

Calibration data KD is created (Block 607) from the obtained complete data set. All respectively required calibration data sets, for example for the separation of the slice scan data sets SMDS into single-slice scan data sets ESMDS, as well as for supplementing non-scanned k-space data within a slice, can be obtained from the calibration data KD according to the undersampling present in each case. The calibration data KD can also be obtained as three-dimensional (3D) calibration data KD with which missing scan points in k-space regarded as three-dimensional in the article by Zahneisen et al. can simultaneously be supplemented.

The acquired slice scan data set SMDS is separated into single-slice scan data sets ESMDS of the simultaneously manipulated slices S1, S2, . . . Sn (Block 609) using the calibration data KD. A parallel acquisition technique can be used here.

Image data of the at least two slices can then be reconstructed (Block 611) from the single-slice scan data sets ESMDS.

If the single-slice scan data sets ESMDS obtained after Block 609 are undersampled according to Nyquist, reconstruction of the image data BD can include completion of the single-slice scan data sets ESMDS using the calibration data KD. In particular, a calibration data set corresponding to the undersampling of the single-slice scan data sets can be created from the calibration data KD, with which set the single-slice scan data sets ESMDS can be supplemented before image data is reconstructed.

The method ends once image data of all desired slices S1, S2, . . . Sn is therefore created ("y", query 613).

If not all of the desired slices have been scanned yet ("n", query 613), the method can be repeated again beginning at Block 601 to acquire the missing data. If a single-shot method is used in which all scan data to be acquired of the manipulated slices is acquired after just one multi-band RF excitation pulse, with a repetition of the method according to steps 601 to 613, a multi-band RF excitation pulse is used which manipulates a group of at least two slices, which have not hitherto been manipulated by a preceding multi-band RF excitation pulse, and whose scan data has not yet been acquired therefore, and from which therefore no image data has hitherto been reconstructed either.

Figure 7:
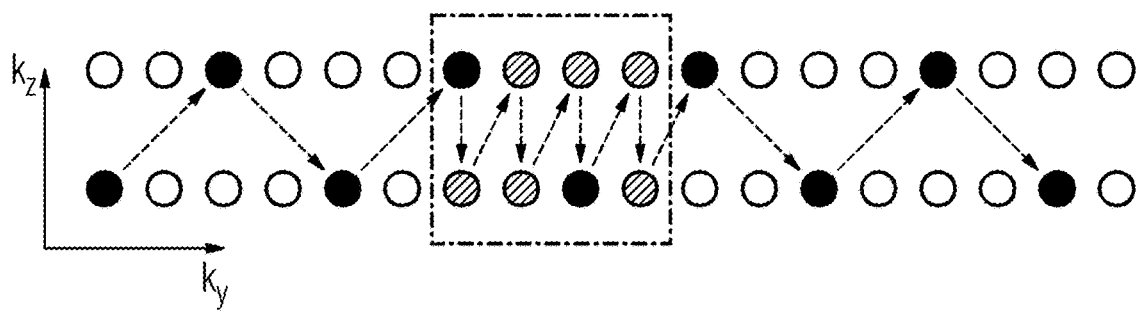
FIG. 7 shows an example of an inventive sampling pattern of k-space.

FIG. 7 is an example of a sampling pattern of k-space as can be used in the inventive method. In the illustrated sampling pattern, k-space points are scanned as slice scan data analogously to an accelerated sampling pattern according to FIG. 5 (scanned points are shown by circles filled in black). In contrast to FIG. 5, a central region of k-space (identified by a broken frame) is completely sampled, however, with at least k-space points shown as hatched circles being additionally acquired as reference data. This can be achieved by scanning every $k_y$ position in the central k-space region twice, wherein, for example, in every other scan of a $k_y$ position, an additional gradient is applied for the shift in the $k_z$ direction. The magnetic resonance data is therefore acquired here according to a CAIPIRINHA method.

The illustrated size of the central k-space region compared to the illustrated sampled k-space region is not representative but is merely for the purpose of improved illustration. The actual size of the central k-space region in which the reference data are acquired, can be defined in a known manner.

In the example shown in FIG. 7 the reference data are therefore acquired interleaved with the slice scan data after a single common multi-band RF excitation pulse. The reference data are initially in the form of slice reference data in which the reference data of the individually scanned slices is overlaid. The slice reference data can be easily separated into reference data for a single one of the acquired slices respectively, for example by a Fourier transform in the $k_z$ direction. The obtained reference data can be inventively used for separation of the acquired slice scan data into single-slice scan data as well as for supplementing undersampled single-slice scan data.

Figure 8:
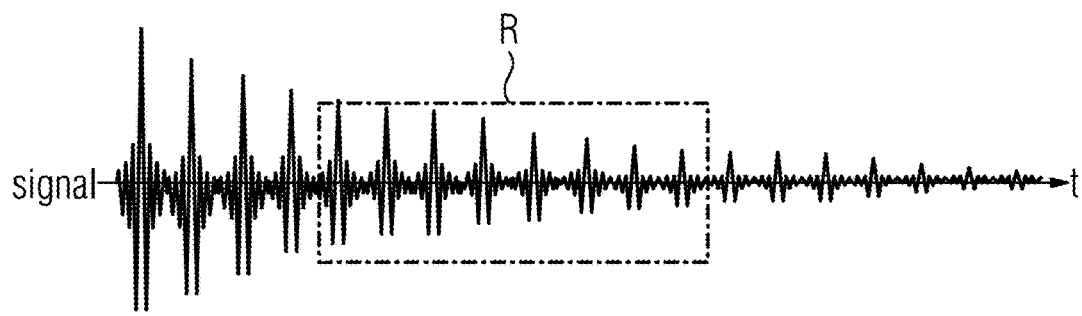
FIG. 8 is shows a schematic illustration of a signal generated with the sampling pattern according to FIG. 7.

FIG. 8 schematically illustrates an exemplary signal in its course over time as can be generated with a sequence following a sampling pattern according to FIG. 7 using a HASTE sequence. The reference data is acquired in the time window identified by R. The strength of the echo signals drops with the decay rate of the transverse magnetization T2.

With interleaved acquisition of this kind of the slice scan data and the reference data using a slice multiplexing method, the reference data and the scan data are inherently acquired under similar conditions, in particular in an identical physiological movement phase and under similar imaging conditions (such as, with identical slice profiles, identical intensity evolutions and/or excitation angle evolutions. As a result, reference data and scan data optimally compliment each other and artifacts can be avoided.

Furthermore, the acquired (slice) reference data can be added to the slice scan data before it is separated into single-slice scan data. The signal-to-noise ratio (SNR) can be improved by this additional scan data.

Figure 9:
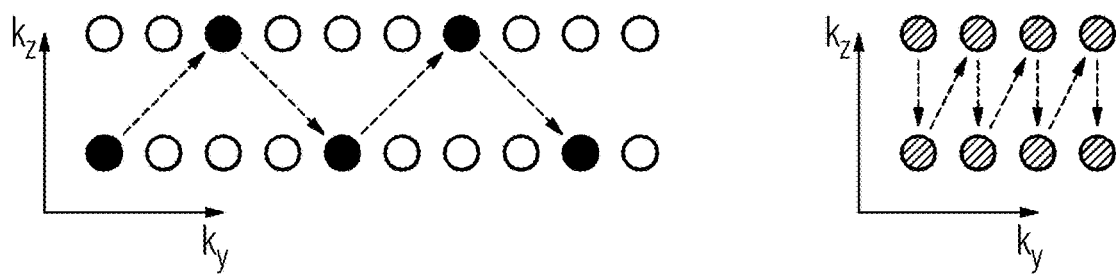
FIG. 9 shows a further example of an inventive sampling pattern of k-space.

FIG. 9 is a further example of a sampling pattern of k-space as can be used in the inventive method. In this example the slice scan data is obtained analogously to FIG. 5 according to the sampling pattern shown on the left with slice multiplexing acceleration (simultaneous manipulation of two slices) and with parallel acquisition acceleration with factor 2 in the $k_y$ direction.

Reference data are acquired (period RD) directly following acquisition of the slice scan data (period MD). For this purpose, after acquisition of the slice scan data, a further, second multi-band RF excitation pulse is radiated which again manipulates the same slices as the multi-band RF excitation pulse, which generated the signals acquired as slice scan data.

The reference data can be acquired according to the sampling pattern illustrated on the right, which shows the central k-space region. A sampling pattern of this kind can be achieved analogously to the process described with reference to the central region of the sampling pattern according to FIG. 7. During acquisition of the reference data, in particular the same sequence type can be used as during acquisition of the slice scan data. For example, if the slice scan data are acquired by a (slice multiplexing) HASTE method, the reference data can likewise be acquired with the use of a (slice multiplexing) HASTE method.

The reference data, which are therefore again present initially as slice reference data, can be separated into reference data of the individual slices with the aid of a Fourier transform, likewise with reference to the example according to FIGS. 7 and 8. The reference data obtained can be inventively used for separation of the acquired slice scan data into single-slice scan data and for supplementing undersampled single-slice scan data.

Figure 10:
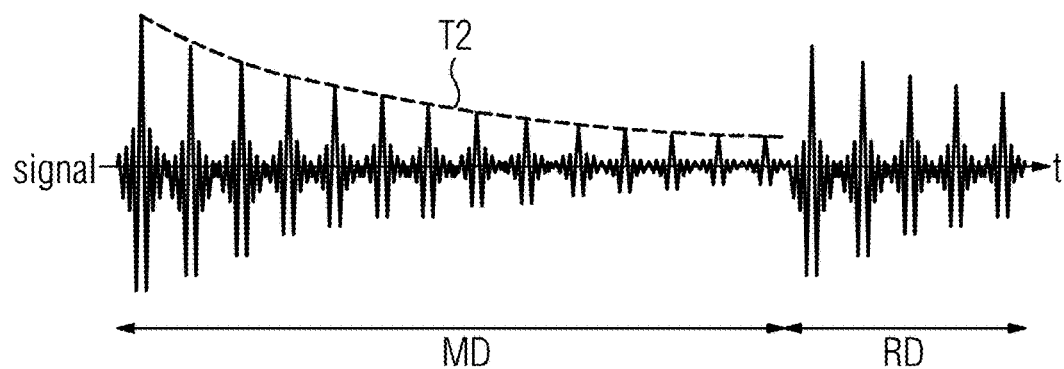
FIG. 10 shows a schematic illustration of a signal generated with the sampling pattern according to FIG. 9.

FIG. 10 schematically illustrates an exemplary signal over time as can be generated with a sequence using a HASTE sequence that follows a sampling pattern according to FIG. 9. The slice scan data is acquired in the time window MD, wherein the strength of the echo signals drops with the decay constant T2. Following acquisition of the slice scan data, the reference data is acquired in the time window RD, which after a renewed multi-band RF excitation pulse firstly has a greater signal strength again which then drops again with T2.

This manner of acquisition of the reference data, which still uses a slice multiplexing method, as slice reference data directly following acquisition of the slice scan data ensures that the reference data are acquired at least in a similar physiological movement phase, since the acquisitions are close together timewise, to the slice scan data. The imaging conditions, in particular the slice profile (since all multi-band RF excitation and refocusing pulses act on the same slices), which exist during acquisition of the reference data, largely match those which existed during acquisition of the slice scan data. The acquisition of the slice scan data in the period MD, which is constantly uniform over the course of time, also contributes to the avoidance of blurring artifacts.

Figure 11:
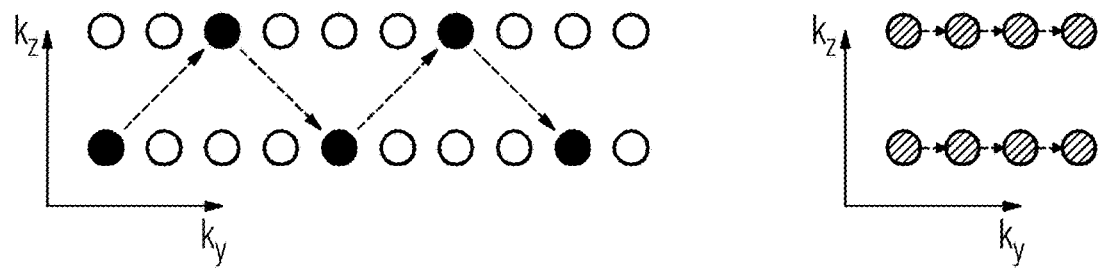
FIG. 11 shows a further example of an inventive sampling pattern of k-space.

FIG. 11 is a further example of a sampling pattern of k-space as can be used in the inventive method.

In this example the slice scan data are again acquired according to the sampling pattern illustrated on the left with slice multiplexing acceleration (simultaneous manipulation of two slices) and with parallel acquisition acceleration of factor 2 in the $k_y$ direction analogously to FIG. 5 and analogously to acquisition of the slice scan data according to FIG. 9.

Reference data are in each case acquired individually for the slices, whose scan data is included in the slice scan data (periods RDS1 and RDS2), directly following acquisition of the slice scan data (period MD). For this purpose, a single-slice RF excitation pulse is radiated after acquisition of the slice scan data, and this excites, for example, a first of the slices manipulated by the preceding multi-band RF pulse, and therefore generates echo signals, which are acquired as reference data RDS1 of this slice. A further single-slice RF excitation pulse is radiated, again directly following acquisition of this reference data of the first slice, which pulse excites a second of the slices manipulated by the preceding multi-band RF pulse, and therefore generates echo signals, which are acquired as reference data RDS2 of this slice. If the slice scan data should contain further slices, further reference data can be analogously acquired for these slices.

The reference data can be acquired for each slice position z according to the sampling pattern illustrated on the right, which shows the central k-space region. During acquisition of the reference data, the same sequence type can be used as during acquisition of the slice scan data. For example, if the slice scan data is acquired by means of a (slice multiplexing) HASTE method, the reference data can likewise be acquired with the use of a (single-slice) HASTE method. The reference data obtained can be inventively used for separation of the acquired slice scan data into single-slice scan data and for supplementing undersampled single-slice scan data.

Figure 12:
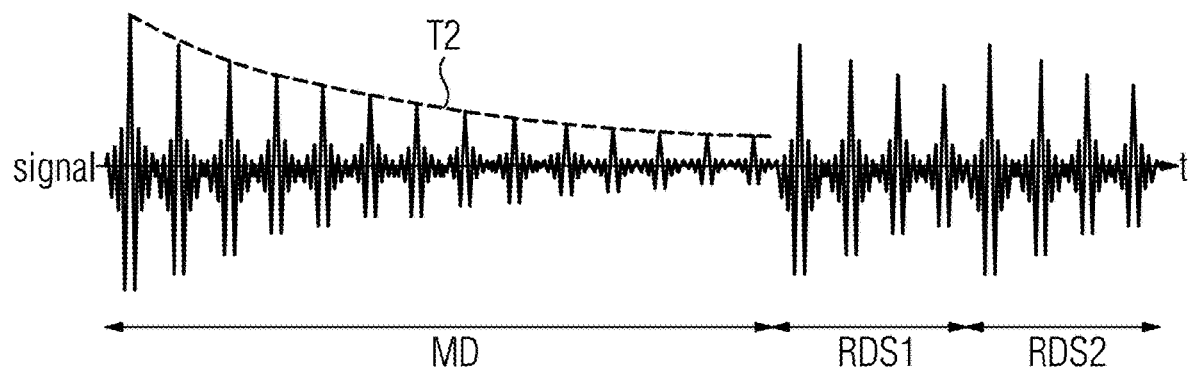
FIG. 12 is a schematic illustration of a signal generated with the sampling pattern according to FIG. 11.

FIG. 12 schematically illustrates an exemplary signal over time as can be generated with a sequence using a HASTE sequence that follows a sampling pattern according to FIG. 11. The slice scan data are acquired in the time window MD, wherein the strength of the echo signals drops with the decay constant T2. The reference data for the individual slices are in each case acquired in the time windows RDS1 and RDS2 following acquisition of the slice scan data. The signal strength also drops here in each case after the associated RF excitation pulse according to the decay constant T2.

This manner of acquisition of the reference data as (single-slice) reference data using single-slice methods again directly following acquisition of the slice scan data, however, ensures that the reference data is acquired at least in a similar physiological movement phase, since the acquisitions are close together in terms of time, as the slice scan data. The acquisition of the slice scan data in the period MD, which is constantly uniform over the course of time, also contributes to the avoidance of blurring artifacts.

The illustrated examples each show, for improved comparison, methods for the acquisition of slice scan data from two slices ("SMS acceleration factor 2") in combination with a further acceleration factor 2 by using parallel acquisition techniques (in other words only every second k-space point in a k-space direction (here: the $k_y$ direction) is acquired). The method can be applied analogously to other SMS acceleration factors and other acceleration factors of the parallel acquisition techniques.

Figure 13:
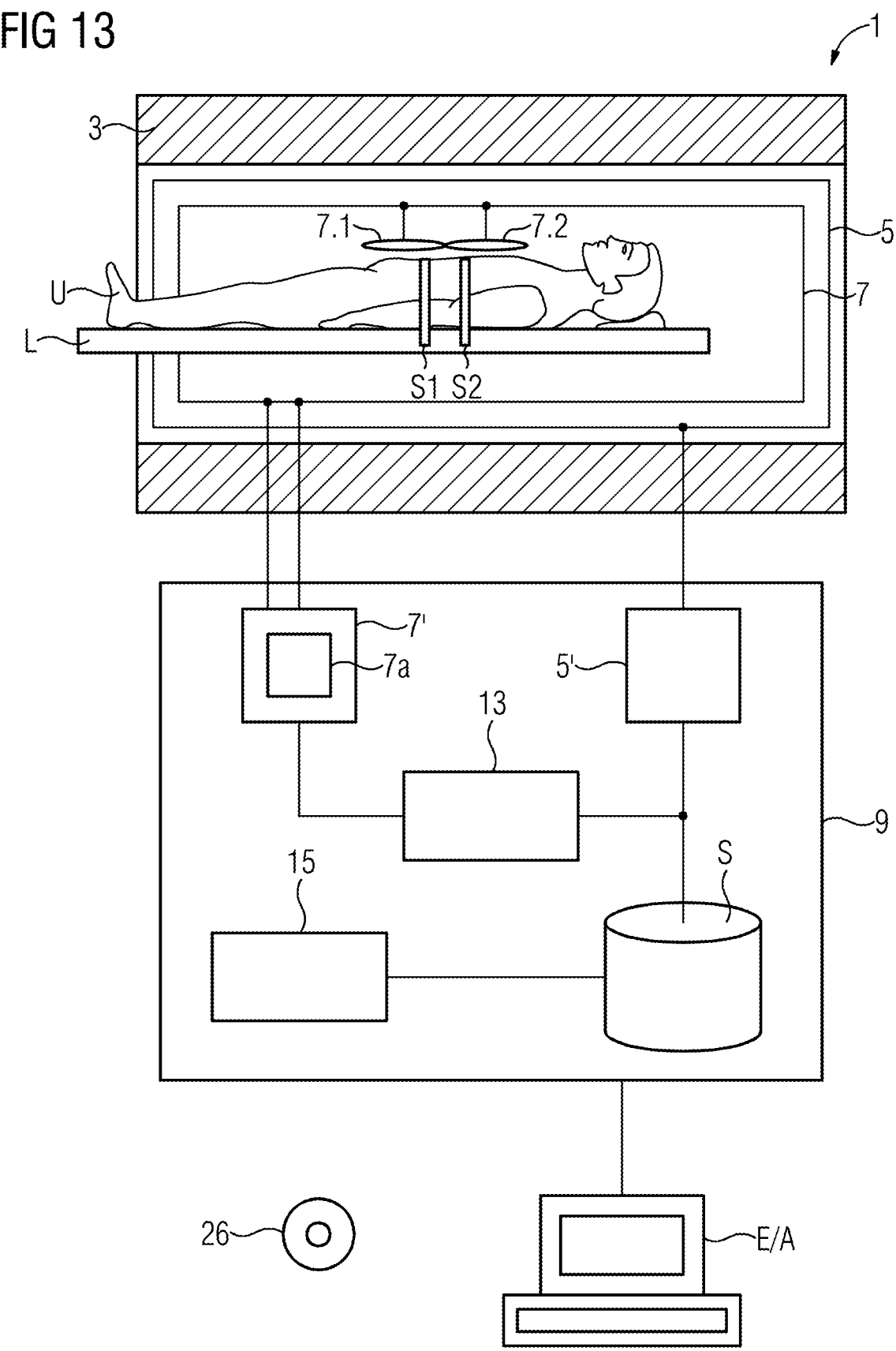
FIG. 13 is a schematic illustration of an inventive magnetic resonance apparatus.

FIG. 13 schematically illustrates an inventive magnetic resonance apparatus 1 that has a scanner 3 that has a basic field magnet that generates the basic magnetic field, a gradient unit 5 for generating the gradient fields, a radio-frequency unit 7 for radiating and for receiving radio-frequency signals, and a control computer 9 designed to execute the inventive method. FIG. 13 illustrates these sub-units of the magnetic resonance apparatus 1 only schematically. In particular, the radio-frequency unit 7 has a number of sub-units, such as at least two coils, as are schematically shown as coils 7.1 and 7.2, which can be configured either just for sending radio-frequency signals, or just for receiving the triggered radio-frequency signals, or for both.

For examination of an examination object U, for example a patient or a phantom, the object can be introduced on a bed L into the scanner 3, into the scanning volume thereof. Slices S1 and S2 constitute examples of two different slices S1 and S2 of the examination object, which can be simultaneously scanned during the acquisition of MR signals.

The control computer 9 controls the magnetic resonance apparatus 1 and can in particular controls the gradient unit 5 via gradient controller 5' and the radio-frequency unit 7 via a radio-frequency transceiving controller 7'. The radio-frequency unit 7 can have multiple channels in which signals can be individually sent or received.

The radio-frequency unit 7, together with its radio-frequency transceiving controller 7', is responsible for the generation and the radiation (transmitting) of a radio-frequency alternating field for manipulation of the spins in a region to be examined (in particular in different slices S1 and S2) of the examination object U. The center frequency of the radio-frequency alternating field, also called the B1 field, is close to the resonance frequency of the spins to be manipulated. Currents controlled by the radio-frequency transceiving controller 7' in the radio-frequency unit 7 are applied to the RF coils to generate the B1 field.

The control computer 9 also has a phase-determining processor 15, for determining phases that are also be inventively impressed.

An arithmetic processor 13 of the control computer 9 is designed to carry out all arithmetic operations required for the necessary scans and determinations. Intermediate results and results required for this this or determined in this connection can be stored in a memory S of the control computer 9. The illustrated units should not necessarily be taken to mean physically separate components. Instead, they merely constitute a subdivision into expedient units but can also be implemented in fewer units or even in just a single physical unit.

Control commands can be conveyed to the scanner 3, and results produced by the control computer 9, such as image data, can be displayed at an input/output device E/A of the magnetic resonance apparatus 1, for example by a user.

A non-transitory, electronically readable data storage medium, in the form of data carrier 26, is provided with programming instructions (program code) stored thereon or therein. The data carrier 26 is loaded into the control computer 9 and thereby causes the control computer 9 to operate the magnetic resonance apparatus 1 according to all of the embodiments that are described above.

Although modifications and changes may be suggested by those skilled in the art, it is the intention of the Applicant to embody within the patent warranted hereon all changes and modifications as reasonably and properly come within the scope of the Applicant's contribution to the art.

The invention claimed is:

1. A method for generating a magnetic resonance (MR) image of an examination object, comprising:
   operating a radio-frequency (RF) radiator of an MR scanner in order to radiate a multi-band RF excitation pulse that simultaneously and selectively manipulates magnetization of nuclear spins in at least two non-overlapping slices of a target volume in the examination object;
   operating the MR scanner so as to acquire echo signals produced by said multi-band RF excitation pulse from said at least two slices, as slice scan data in a slice scan data set, said slice scan data set comprising scan data for all simultaneously manipulated slices of the target volume;

operating the MR scanner so as to acquire reference data for said at least two non-overlapping slices, with reference data for each respective slice scan data set being acquired by, between acquisition of the slice scan data of the respective slice scan data set, and acquisition of the reference data associated therewith, no scan data of slices being acquired that are not included in said at least two non-overlapping slices of the respective slice scan data set;

entering the slice scan data for each slice scan data set together with the reference data therefor into a memory organized as k-space, by filling a central region of k-space with said slice scan data for a respective slice scan data set and the associated reference data forming a completely scanned data set, according to the Nyquist criterion, in said central region of k-space;

in a computer, accessing said completely scanned data set from said memory and generating calibration data from said completely scanned data set;

in said computer, using said calibration data to separate the slice scan data set into single-slice scan data sets respectively for the at least two non-overlapping slices; and reconstructing respective image data sets from the respective single-slice scan data sets, and making the image data sets available in electronic form from the computer.

2. A method as claimed in claim 1 comprising reconstructing said image data sets by completing said single-slice scan data sets using said calibration data.

3. A method as claimed in claim 1 comprising acquiring all echo signals for an individual slice scan data set after radiating a single multi-band RF excitation pulse.

4. A method as claimed in claim 1 comprising operating said MR scanner according to a CAIPIRINHA method in order to acquire said slice scan data.

5. A method as claimed in claim 1 comprising operating said MR scanner according to a turbo spin echo method in order to acquire said slice scan data.

6. A method as claimed in claim 5 comprising operating said MR scanner according to a HASTE sequence, as said turbo spin echo sequence.

7. A method as claimed in claim 1 comprising acquiring said reference data interleaved with the slice scan data for the respective slice scan data set associated with the reference data.

8. A method as claimed in claim 1 comprising acquiring said reference data for a respective slice scan data set after acquisition of the slice scan data for that respective slice scan data set.

9. A method as claimed in claim 8 comprising acquiring said reference data as slice reference data after radiating a further multi-band RF pulse that simultaneously and selectively manipulates the nuclear spins of said at least two non-overlapping slices.

10. A method as claimed in claim 9 comprising separating said slice reference data into slice-specific reference data sets, each comprising only reference data of one of said at least two non-overlapping slices.

11. A method as claimed in claim 8 comprising acquiring said reference data for a respective slice scan data set after radiating multiple single-slice RF excitation pulses that respectively individually manipulate nuclear spins only in one of said at least two non-overlapping slices.

12. A magnetic resonance (MR) apparatus comprising:
an MR data acquisition scanner comprising a radio-frequency (RF) radiator;

a control computer configured to operate said RF radiator in order to radiate a multi-band RF excitation pulse that simultaneously and selectively manipulates magnetization of nuclear spins in at least two non-overlapping slices of a target volume in an examination object situated in said MR data acquisition scanner;

said control computer being configured to operate the MR scanner so as to acquire echo signals produced by said multi-band RF excitation pulse from said at least two slices, as slice scan data in a slice scan data set, said slice scan data set comprising scan data for all simultaneously manipulated slices of the target volume;

said control computer being configured to operate the MR scanner so as to acquire reference data for said at least two non-overlapping slices, with reference data for each respective slice scan data set being acquired by, between acquisition of the slice scan data of the respective slice scan data set, and acquisition of the reference data associated therewith, no scan data of slices being acquired that are not included in said at least two non-overlapping slices of the respective slice scan data set;

a memory;

said control computer being configured to enter the slice scan data for each slice scan data set together with the reference data therefor into said memory, organized as k-space, by filling a central region of k-space with said slice scan data for a respective slice scan data set and the associated reference data forming a completely scanned data set, according to the Nyquist criterion, in said central region of k-space;

a reconstruction computer configured to access said completely scanned data set from said memory and to generate calibration data from said completely scanned data set;

said reconstruction computer being configured to use said calibration data to separate the slice scan data set into single-slice scan data sets respectively for the at least two non-overlapping slices; and said reconstruction computer being configured to reconstruct respective image data sets from the respective single-slice scan data sets, and to make the image data sets available in electronic form from the reconstruction computer.

13. A non-transitory, computer-readable data storage medium encoded with programming instructions, said storage medium being loaded into a computer system of a magnetic resonance (MR) apparatus comprising an MR scanner with a radio-frequency (RF) radiator, said programming instructions causing said computer system to:

operate the RF radiator in order to radiate a multi-band RF excitation pulse that simultaneously and selectively manipulates magnetization of nuclear spins in at least two non-overlapping slices of a target volume in the examination object situated in the MR data acquisition scanner;

operate the MR scanner so as to acquire echo signals produced by said multi-band RF excitation pulse from said at least two slices, as slice scan data in a slice scan data set, said slice scan data set comprising scan data for all simultaneously manipulated slices of the target volume;

operate the MR scanner so as to acquire reference data for said at least two non-overlapping slices, with reference data for each respective slice scan data set being acquired by, between acquisition of the slice scan data of the respective slice scan data set, and acquisition of the reference data associated therewith, no scan data of slices being acquired that are not included in said at least two non-overlapping slices of the respective slice scan data set;

enter the slice scan data for each slice scan data set together with the reference data therefor into a memory organized as k-space, by filling a central region of k-space with said slice scan data for a respective slice scan data set and the associated reference data forming a completely scanned data set, according to the Nyquist criterion, in said central region of k-space;

access said completely scanned data set from said memory and generate calibration data from said completely scanned data set;

use said calibration data to separate the slice scan data set into single-slice scan data sets respectively for the at least two non-overlapping slices; and reconstruct respective image data sets from the respective single-slice scan data sets, and make the image data sets available in electronic form from the computer system.

* * * * *